United States Patent [19]

LaCourse et al.

[11] Patent Number: 5,350,593
[45] Date of Patent: Sep. 27, 1994

[54] DIETARY FIBER DERIVED FROM TAPIOCA AND PROCESS THEREFOR

[75] Inventors: Norman L. LaCourse, Indianapolis, Ind.; Karen Chicalo, Marlton, N.J.; James P. Zallie, Hillsborough, N.J.; Paul A. Altieri, Belle Mead, N.J.

[73] Assignee: National Starch and Chemical Investment Holding Corporation, Wilmington, Del.

[21] Appl. No.: 157,489

[22] Filed: Nov. 23, 1993

Related U.S. Application Data

[63] Continuation of Ser. No. 812,559, Dec. 23, 1991, abandoned.

[51] Int. Cl.$^5$ .......................................... A23L 1/0522
[52] U.S. Cl. ..................................... 426/615; 426/49; 426/52; 426/253; 426/481; 426/495; 426/506; 426/626; 426/627; 426/640
[58] Field of Search ............... 426/49, 52, 253, 481, 426/495, 506, 626, 627, 640, 615

[56] References Cited

U.S. PATENT DOCUMENTS

| | | | |
|---|---|---|---|
| 1,543,458 | 6/1925 | Takamine, Jr. | 426/627 |
| 4,241,093 | 12/1980 | Farag et al. | 426/258 |
| 4,649,113 | 3/1987 | Gould | 435/165 |
| 4,759,942 | 7/1988 | Von Fulger | 426/621 |
| 4,774,099 | 9/1988 | Feeney | 426/552 |
| 4,804,545 | 2/1989 | Goering et al. | 426/52 |
| 4,806,475 | 2/1989 | Gould | 435/165 |
| 4,844,924 | 7/1989 | Stanley | 426/258 |
| 4,923,709 | 5/1990 | Slimak | 426/640 |
| 4,948,600 | 8/1990 | Zumbé et al. | 426/52 |
| 5,169,662 | 12/1992 | Spicer | 126/449 |

FOREIGN PATENT DOCUMENTS

| | | |
|---|---|---|
| 1074088 | 1/1988 | Australia . |
| 2353232 | 10/1975 | France . |
| WO91/15967 | 10/1991 | PCT Int'l Appl. . |
| 1291547 | 5/1971 | United Kingdom . |
| 2134767 | 2/1984 | United Kingdom . |

OTHER PUBLICATIONS

Whistler, R. 1984. Starch:Chemistry and Technology. Academic Press, Inc. N.Y. p. 88.
S. Budavari, et al., "The Merck Index", Eleventh Edition, 1989, Merck & Co., Rahway, N.J. p. 1216.
Corbishley, Douglas A., "Tapioca, Arrowroot, and Sago Starches: Production,"Starch, 2nd ed., Academic Press, Inc., Chaper XIII, pp. 469–478 (1984).
Balagopalan, C., Ph.D., et al., "Cassava in Food, Feed, and Industry," CRC Press, Inc., Florida (1988) pp. 54–55, 59–62, 97–111, 161.
Brough, S. H., et al., "Characterisation of the Dietary Fiber of Cassava," R. Soc. Chem., 83:133–135 (1990).
N. P. Ghildyal and B. K. Lonsane, "Utilization of Cassava Fibrous Residue for the Manufacture of Value-added Products: An Economic Alternative to Waste Treatment," Process Biochemistry, Apr. 1990, pp. 35–39.
"USDA's Oatrim Replaces Fat in Many Food Products", Food Technology, Oct., 1990, p. 100.
Food Chemical News, May 7, 1990, "Barley Hailed as Cereal Grain of the '90s, by Newman".
Peter M. Ranum, et al., "Bleaching of Flour and Dietary Fiber Products", Cereal Foods World, Dec., 1989, 34:984–985 and 988.
Alfred Olsen, et al.,"Chemistry and Analysis of Soluble Dietary Fiber",Food Technology, Feb. 1987, pp. 71–80.
Barbara O. Schneeman, "Soluble vs Insoluble Fiber—Different Physiological Responses", Food Technology, Feb., 1987, pp. 81–82.

Primary Examiner—Helen Pratt
Attorney, Agent, or Firm—Ellen T. Dec

[57] ABSTRACT

Dietary fiber are derived from the tapioca pulp fiber that is a by-product of tapioca starch milling operations. The tapioca fiber may be refined through an enzymatic destarching step to provide a fiber comprising at least 70% total dietary fiber, of which at least 12% is soluble dietary fiber. The fiber may be further refined by bleaching. Acceptable foods may be prepared comprising unrefined or refined tapioca fiber.

15 Claims, No Drawings

5,350,593

DIETARY FIBER DERIVED FROM TAPIOCA AND PROCESS THEREFOR

This application is a continuation of U.S. application Ser. No. 07/812,559, filed Dec. 23, 1991, abandoned.

This invention relates to refined dietary fiber products derived from tapioca and to an enzymatic process for refining the fiber. This invention also relates to foods that are nutritionally fortified with dietary fiber, either refined or crude, obtained from tapioca sources.

BACKGROUND OF THE INVENTION

High fiber diets have been promoted over the past several years because of the potential health benefits they offer. High fiber diets are reported to reduce the risk of colon and rectal cancers and to reduce blood serum cholesterol levels. Because dietary fiber is not well digested by humans, dietary fiber ingredients are non-caloric and contribute to a reduction in total food calories to the extent that they are used as a replacement for caloric ingredients such as carbohydrates, proteins, and fats.

The total dietary fiber (TDF) of a food or a food ingredient comprises two components: soluble dietary fiber (SDF) and insoluble dietary fiber (IDF). It is reported that the soluble dietary fiber component is the critical component in reducing serum cholesterol. It is reported that insoluble dietary fiber health benefits achieved by consuming the fiber.

A number of dietary fibers are presently marketed as ingredients for use in formulating "healthy" food products. These fiber-containing, nutritionally-fortified, food ingredients are characterized by different fiber contents, with the highest percentage of SDF (70%) reported for Psyllium and the highest TDF (99%) reported for alpha-cellulose. The dietary fiber contents of other fiber sources are: beet fiber (75% TDF; 24% SDF); corn bran (90% TDF; 2% SDF); oat bran (20-25% TDF; 12% SDF); refined oat bran (97% TDF; 1% SDF); rice bran (27-35% TDF; 2-6% SDF); wheat bran (40% TDF; 0% SDF); pea fiber (45% TDF; 5% SDF); potato fiber (75% TDF; 15-20% SDF); Psyllium husk (87% TDF; 70% SDF); and soy fiber (75% TDF; 15% SDF).

It has been discovered that tapioca fiber, which is a by-product of the tapioca starch milling process, may be refined by the removal of residual starch to yield a refined fiber containing approximately 70% TDF and 12% SDF. The crude tapioca fiber or pulp which is the direct by-product of starch milling contains approximately 67% starch, 30% TDF and 5% SDF, on a dry-weight basis. The tapioca root in various forms (e.g., cassava or manioc; poi (Hawaii); and farina (South America and the West Indies) has been used as a source of starch in the human diet.

It has been discovered that by destarching the unrefined tapioca fiber by-product, a bland, functionally compatible dietary fiber high in TDF and SDF may be obtained. Most fiber refining processes yield high TDF and IDF levels but reduce SDF levels. Thus, it is unexpected that a product containing high amounts of both fibers may be achieved by refining a raw fiber source.

As a further advantage, it has been discovered that the unrefined tapioca fiber (as well as the refined fiber) may be used in certain human foods (e.g., cereals) wherein its unique starch and fiber components provide functional benefits to the foods.

Many foods in the bread and cereal product group are nutritionally fortified by the addition of various fibers. Serious functional problems are frequently encountered in formulating foods containing high fiber ingredients. These problems include off-flavors and colors contributed by the fiber ingredient, together with textural problems such as lack of volume or expansion in baked goods or cereals, non-uniform texture, unpredictable water holding and/or absorption characteristics, interference with the production of extruded and expanded cereals or snacks, and other related problems.

One solution to these problems has been to refine the fiber so as to eliminate the color, flavor and non-uniform texture problems. However, the refinement process usually eliminates the SDF component of the fiber.

Other means that have been suggested for formulating foods with high fiber content include preparing a fiber ingredient to contain a specific particle size to provide a food having a density within a specified range. For example, U.S. Pat. No. 4,759,942, issued Jul. 26. 1988, to Von Fulger, discloses a process for producing a high fiber breakfast cereal, wherein the fiber is used at 3-9% of the cereal and the fiber is a bran (obtained from the outer layer of grains) material having an average particle size from 5-100 microns which produces an extruded cereal having a specific density of from 0.15 to 0.40 g/cc.

It is now been found that by employing an enzymatic process to refine tapioca fiber, the SDF content of the fiber is maintained and the components of the unrefined tapioca fiber which add caloric value or detract from its use in food formulation are effectively removed. The enzymatic destarching process may be combined with a bleaching process which also preserves the SDF content of the fiber while improving its functional characteristics, and it may be combined with particle size control to improve texture and color. Thus, a food ingredient is provided which may be used to nutritionally fortify a variety of food products by providing high TDF and SDF contents.

It has also been found that in contrast to bran derived from grains. unrefined tapioca pulp fiber may be used to fortify cereals without having an unacceptable impact on cereal functionality or quality.

SUMMARY OF THE INVENTION

This invention provides a dietary fiber of tapioca origin, comprising, on a dry solids basis, at least 70% total dietary fiber, of which at least 12% is soluble dietary fiber, and less than 15% starch.

This invention also provides a process for refining tapioca fiber obtained from a tapioca pulp by-product of starch milling operations, the process comprising the steps:

(a) slurrying from 5 to 10%, by weight, ground tapioca pulp in an aqueous media;

(b) enzymatically treating the slurry with a 1,4-alpha-D-glucosidase to depolymerize sufficient starch to yield a tapioca fiber containing less than 15% starch;

(c) separating the tapioca fiber from the slurry; and (d) washing the tapioca fiber, wherein the refined tapioca fiber contains at least 70% total dietary fiber, of which at least 12% is soluble dietary fiber. The process may further comprise the step of bleaching the tapioca fiber with a reagent selected from hydrogen peroxide, sodium chlorite, sodium hypochlorite and potassium permanganate. The destarching and bleaching steps may be followed by the steps of drying the fiber to a moisture content of less than 15% and grinding the fiber to a smaller, more uniform particle size wherein 95% of the particles pass through a U.S.S.S. 100 mesh screen.

This invention also provides nutritionally fortified, fiber-containing foods, comprising at least one dietary fiber of tapioca origin selected from unrefined tapioca fiber, refined tapioca fiber, and bleached, refined tapioca fiber. These foods include bread and other baked goods, fried foods, breaded and coated foods, and cereals.

DESCRIPTION OF THE PREFERRED EMBODIMENTS

The term "tapioca" is commonly used to refer to both the tapioca (or cassava) plant and the granular starch that is extracted from the tapioca plant. The tapioca plant is a member of the Euphorbiaceae or spurge family, manihot genus. Tapioca starch in granular form has been traditionally used in puddings and as a thickener in liquid foods. It is considered to have a very mild flavor and to be suitable for hypoallergenic foods. The tapioca starch is obtained from the tuberous root of the tapioca plant.

Tapioca pulp fiber is a by-product of the tapioca starch milling operation. The unrefined tapioca fiber is typically air-dried and sold as animal feed. The unrefined fiber contains about 60%, by weight, starch, 30%, by weight, TDF, and 5%, by weight, SDF. As a by-product of the starch manufacturing operation, tapioca fiber may comprise the residue of the peel or outer skin, the inner rind or core, and the other fibrous components of the tuber. Following milling and extraction of the starch from the tuberous root, the tapioca fiber is in the form of a slurry which is generally dried to reduce microbial activity. Any of a variety of processing steps (e.g., washing, pulverizing, sifting, drying, rinsing, and other steps) may be carried out on the root in its raw state or on the residual pulp used to produce the tapioca fiber. Additionally, the tapioca fiber may be treated with various food grade anti-microbial reagents (e.g., hydrogen peroxide, peracetic acid, and sodium chlorite) to prevent microbial activity. In a preferred embodiment, microbial and metal or mineral contaminants may be removed by treating an aqueous slurry of the pulp with peroxide for 6 hours at a pH of 5.4 and then with a solution of ethylene diamine tetraacetic acid for 4 hours at a pH of 4.5, followed by washing and drying.

After the fiber has been isolated from the tapioca root, the fiber may be refined by the process disclosed herein. To reduce the caloric content of the tapioca fiber and to increase the relative proportions of TDF and SDF, the tapioca fiber is treated with an enzyme which depolymerizes the starch so that the depolymerized starch residue may be easily removed from the fiber by an aqueous wash. In this enzymatic treatment, the starch content of the tapioca fiber may be decreased from about 60% to about 15%, and preferably 5%, by weight.

The destarching process is carried out with an alpha-amylase enzyme. The enzyme may be derived from any source. A heat stable alpha-amylase, such as Termamyl® enzyme (obtained from Novo Laboratories, Inc., Denmark) may be used at temperatures of 40°-95° C. with greatest activity at 90° C. In a preferred embodiment, a 7% solids slurry of unrefined tapioca fiber may be destarched (using the enzyme at 1%, by weight, of unrefined tapioca fiber) in 4 hours at a temperature of 90° C. and a pH of 6.5. The enzyme may be deactivated by lowering the pH to about 2.0 with sulfuric acid and holding it at the lowered pH for 15 minutes. Thereafter, the pH may be raised by the addition of sodium hydroxide or other base to a pH of about 5.0 to 7.0. The destarched tapioca fiber may be filtered, washed and oven-dried or air-dried, at about 50° C. to 60° C. for 1 to 2 days.

The tapioca fiber may also be destarched by treatment with enzymes that are only stable at temperatures below 80° C. For example, a 7% solids slurry of the unrefined tapioca fiber may be treated at 70° C. for 4 hours with BAN® alpha-amylase (used at 1%, by weight, of unrefined tapioca fiber) at a pH of 6.5 for 4 hours. The enzymatic reaction is carried out with constant agitation. Following the destarching operation, the enzyme may be deactivated by lowering the pH as described previously. Thereafter, the pH may be adjusted to about 5.0 to 7.0 with sodium hydroxide or other base and the destarched fiber filtered, washed and dried.

In another preferred embodiment, a glucoamylase enzyme may be employed to destarch the tapioca fiber. The glucoamylase is typically used at about 50° C. for about 4 hours. The tapioca fiber may be cooked for 45 minutes at 100° C. in a boiling water bath to make the starch more accessible to glucoamylase activity. The cooked tapioca fiber dispersion should be cooled to 50° to 60° C. before addition of the enzyme. The enzyme may be used at about 1%, by weight, of tapioca fiber, with agitation and under the pH and other conditions described above for other amylases.

The amount of starch remaining in the tapioca fiber following the destarching process may be determined by optical rotation using a polarimeter.

The enzymatic destarching process may be combined with other treatments so as to provide a fiber having various degrees of refinement. For example, the enzymatic treatment may be combined with an acid treatment, provided that the TDF and SDF content of the fiber is not significantly altered. The combined enzyme/acid treatment may improve the rate of destarching and the functional characteristics of the fiber following processing. Other treatments, such as bleaching, filtering, drying, and the like may be combined with the enzymatic treatment. The types of processes may be selected by one skilled in the art so as to produce a particular fiber for a particular end use application (e.g., the fiber appropriate for use in cakes, breads and other delicate baked goods may require more refinement than the fiber used in flaked cereal products).

When a bleaching step is combined with the enzymatic treatment, the bleaching step generally is conducted after enzymatic treatment. Additionally, either the crude, unrefined tapioca fiber or the destarched tapioca fiber may be subjected to the bleaching treatment. While any food bleaching agent may be employed, it has been discovered that certain bleaching agents are more effective in providing tapioca fiber of a light color. Among the more effective bleaching agents are peracetic acid, sodium chlorite, sodium hypochlorite, and potassium permanganate.

In applications where the SDF content is not critical, it is possible to bleach the tapioca fiber using a process such as the process disclosed in U.S. Pat. No. 4,649,113, issued Mar. 10, 1987 to Gould, or U.S. Pat. No.

4,806,475, issued Feb. 21, 1989, to Gould wherein the fiber is pretreated with hydrogen peroxide at a high pH to reduce the lignin content. The process disclosed in U.S. Pat. No. 4,844,924, issued Jul. 4, 1989 to Stanley, may be used to esterify the color-causing components of the fiber (e.g., the lignin) by treatment with a reagent such as acetic anhydride, followed by bleaching.

After the tapioca fiber has been refined to the desired degree, the fiber may be dried by any method known in the art. In a preferred embodiment, the tapioca fiber, either in refined or unrefined form, is dried from about 80% moisture to about 10 to 15% moisture by oven drying, flash-drying, air-drying, or spray-drying.

Following drying, the tapioca fiber may be ground to a particular particle size. For most food applications, a particle size wherein 95% of the particles pass through a U.S.S.S. 100 mesh screen is preferred.

The tapioca fiber, in its crude, destarched, or bleached form may be used in food applications at about 1% to 43%, by weight, of the food. The amount of fiber used should be an amount effective to fortify the food with fiber, so as to maximize health benefits in the diet. The amount of tapioca fiber used in any given food will be determined to a great extent by the amount that can be tolerated from a functional standpoint. In other words, the amount of fiber used generally will be as high as will be acceptable in organoleptic evaluation of the food. Due to its unique character, tapioca fiber can generally be used in foods at levels higher than fibers obtained from other sources.

In cereals, including ready-to-eat flaked, puffed or expanded cereals and cereals which are cooked before eating, the tapioca fiber may be used at 5 to 43%, by weight, of the dry cereal.

In baked goods, the refined, destarched and bleached tapioca fiber is generally used at about 2 to 7%, by weight, of the baked good. Baked goods include breads, crackers, muffins, cakes, cookies, rolls, pastries, and other baked goods that primarily comprise flour, starch and other grain-based ingredients.

In coated or breaded foods, the tapioca fiber may be used at 5 to 15%, by weight on a dry basis, of the coating or breading material. The fiber may be blended with the other coating components and used as a blend, or the fiber may be incorporated into the bread or cracker dough prior to cooking, grinding and use as a bread crumb or other particular matter within the coating or breading mix.

In fried foods, such as farinaceous-based snacks, doughnuts and fried breadings, the tapioca fiber may be used at 1 to 5%, by weight, of the fried food. The tapioca fiber reduces the oil uptake that is typical of flours, starches and other farinaceous materials generally used in the typical fried food formulation. The tapioca fiber will absorb and hold water and sufficient oil or fat to provide an organoleptically acceptable food product. The selection of a fiber for use in food may depend upon the degree of refinement of the fiber and the water holding capacity, viscosity and oil- or water-absorption characteristics of the fiber. For example, the high water holding capacity of the destarched, bleached tapioca fiber has a beneficial effect when the fiber is incorporated into breads and muffins. The benefit is realized as a desirable, moist texture in the bread, muffin or other baked goods that have been formulated with the fiber.

In a preferred embodiment one serving of the food comprises at least 4 grams of total dietary fiber of tapioca origin, of which fiber at least 10%, by weight, is soluble dietary fiber.

EXAMPLE 1

This example illustrates the preparation of destarched tapioca fiber.

Part A

A sample of unrefined tapioca pulp (80% moisture) obtained from National Starch & Chemical (Thailand) Ltd., Bangkok, Thailand, was slurried at 7% solids in water. The pH of the slurry was adjusted to 6.5 with a 3% sodium hydroxide or 3:1 sulfuric acid solution; alpha-amylase (Termanyl® 120L enzyme obtained from Novo Laboratories, Inc., Denmark) was added at 1%, by weight of tapioca pulp, to the slurry; and the enzyme was permitted to digest the starch under the conditions described in Table I with constant agitation of the slurry.

The enzyme was deactivated by lowering the pH of the slurry to 2.0 for 15 minutes with a 3:1 sulfuric acid solution. The pH was adjusted to 5.5 with a 3% sodium hydroxide solution; the slurry was filtered through 2 layers of cheese cloth in a Buchner funnel and washed, with 1.5X the volume of water present in the slurry, and the filter cake was oven-dried at 50°–60° C. for 1 to 2 days.

TABLE I

| COMPOSITION OF TAPIOCA FIBER AFTER DESTARTCHING REACTION[a] | | | | | | | |
|---|---|---|---|---|---|---|---|
| Sample # | Reaction Time (Hrs.) | Reaction Temp (°C.) | Washed | Starch % (dry wt.) | TDF %[b] (dry wt.) | SDF %[c] (of TDF) | Brabender[d] Viscosity (BU) |
| Control | — | — | — | 55–68 | 25–35 | 3–7 | 200 |
| 1 | 4 | 100 | no | 25 | — | — | 60 |
| 2 | 4 | 100 | yes | 7.3 | — | — | — |
| 3 | 4 | 100 | no | — | 63.3 | 9.8 | — |
| 4 | 4 | 100 | yes | — | 74.7 | 14.7 | 350 |
| 5 | 4 | 100 | no | — | 67.2 | 13.1 | — |
| 6 | 4 | 100 | yes | — | 79.4 | 20.7 | — |
| 7 | 4 | 80 | no | 6.4 | 77.3 | 27.0 | — |
| 8 | 4 | 80 | yes | 2.7 | 86.0 | 26.0 | — |
| 9[e] | 0.5/3.5 | 100/70 | no | 16.8 | 67.2 | 8.9 | — |
| 10[e] | 0.5/3.5 | 100/70 | yes | 3.1 | 81.2 | 17.4 | — |
| 11 | 4 | 80 | yes | 5.5 | — | — | 85 |
| 12 | 4 | 80 | yes | — | — | — | — |
| 13 | 4 | 80 | yes | — | — | — | — |
| 14 | 4 | 80 | yes | 2.14 | — | — | — |
| 15 | 0.5 | 80 | yes | 29.90 | — | — | 20 |
| 16 | 0.5 | 80 | no | 50.27 | — | — | — |
| 17 | 1.0 | 80 | yes | 8.70 | — | — | 100 |
| 18 | 1.0 | 80 | no | 45.95 | — | — | — |

TABLE I-continued

COMPOSITION OF TAPIOCA FIBER AFTER DESTARTCHING REACTION[a]

| Sample # | Reaction Time (Hrs.) | Reaction Temp (°C.) | Washed | Starch % (dry wt.) | TDF %[b] (dry wt.) | SDF %[c] (of TDF) | Brabender[d] Viscosity (BU) |
|---|---|---|---|---|---|---|---|
| 19 | 2.0 | 80 | yes | 8.20 | — | — | 300 |
| 20 | 2.0 | 80 | no | 17.30 | — | — | — |
| 21 | 3.0 | 80 | yes | 7.00 | — | — | 50 |
| 22 | 3.0 | 80 | no | 35.14 | — | — | — |
| 23 | 4.0 | 80 | yes | 2.30 | — | — | 1500 |
| 24 | 4.0 | 80 | no | 28.02 | — | — | — |
| 25 | 5.0 | 80 | yes | 3.20 | — | — | 1000 |

[a]See Example 1, Part A.
[b]Total dietary fiber.
[c]Soluble dietary fiber expressed as a percentage, on a dry weight basis, of total dietary fiber.
[d]Brabender measurements were taken at 5% solids, and 92° C. for 10 minutes.
[e]Samples 9 and 10 were treated for 0.5 hours at 100° C. and then for 3.5 hours at 70° C.

STARCH CONTENT

The percentage of starch present in tapioca fiber samples was measured using a polarimeter (Model 141, obtained from Perkin-Elmer, Norwalk, Connecticut). This procedure is a modification of the "Feedstuffs Analysis Procedure for Starch" (G-28) of the *Standard Analytical Methods of the Member Companies of the Corn Refiners Association, Inc.*, Second Revision, April 15, 1986. In this modified procedure, a 2%, by weight, solution of tapioca fiber in 40% dihydrate calcium chloride solution was cooked in a beaker in a boiling water bath for 30 minutes. The beaker contents were restored to their original weight by the addition of the calcium chloride solution and the sample was filtered on a Buchner funnel fitted with glass fiber filter paper. The filtrate was collected and the optical rotation of the filtrate was measured with a polarimeter.

TOTAL DIETARY FIBER

The percentage of total dietary fiber present in tapioca fiber samples was measured by the AACC Method 32-05. *American Association of Cereal Chemists*, Revised Nov. 1, 1989.

SOLUBLE DIETARY FIBER

The percentage of soluble dietary fiber present in tapioca fiber samples was measured by the difference between the total dietary fiber method (AACC method #32-05) and the neutral detergent method (AACC method #32-20). *American Association of Cereal Chemists*, Revised Oct. 27, 1982.

BRABENDER VISCOSITY

The viscosities of 5% anhydrous solids slurries of the tapioca fiber samples were measured on a Brabender Visco-amylograph (Model VA1B, obtained from C. W. Brabender Instruments, Inc., South Hackensack, NJ) fitted with a 350 cmg cartridge at a pH of 6.5. The samples were heated rapidly to 50° C., then control heated to 92° C. and held at 92° C. for 10 minutes.

Part B

The unrefined tapioca pulp was destarched as in Part A, except that the 7% slurry of tapioca pulp was treated with a 3% sodium hydroxide solution (molar concentration=0.75) for a ½ hour to gelatinize the starch and a different alpha-amylase enzyme (Ban ® 120L enzyme, obtained from Novo Laboratories, Inc., Denmark) was used for destarching. All samples were washed as in Part A, above. Experimental variables and product characteristics are shown in Table II.

Part C

The unrefined tapioca pulp was destarched as in Part A, except that the slurry was cooked at 100° C. in a boiling water bath for 30 minutes to gelatinize the starch and a different alpha-amylase enzyme (glucoamylase, obtained from Novo Laboratories, Inc., Denmark) was added to the cooked slurry at 1%, by weight of tapioca pulp. The product was washed. Experimental variables and product characteristics are shown in Table II.

TABLE II

ENZYME TREATMENTS OF UNREFINED TAPIOCA FIBER[a]

| Sample | Enzyme | Reaction Time (Hrs.) | Reaction Temp. (°C.) | Starch % (dry wt.) | TDF %[b] (dry wt.) | SDF %[c] (of TDF) | Brabender[d] Viscosity (BU) | Color of Product |
|---|---|---|---|---|---|---|---|---|
| Control | — | — | — | 55–68 | 25–35 | 3–7 | 150 | Tan |
| 26 | Ban 120L | 4 | 70 | 10.6 | — | — | 115 | Brown |
| 27 | Ban 120L | 4 | 70 | — | — | — | — | Brown |
| 28 | Ban 120L | 4 | 65 | 18.50 | — | — | — | Brown |
| 29[e] | Glucoamylase | 0.5/3.5 | 100/50 | 14.1 | — | — | 100 | Brown |

[a]See Example 1, Part B and Part C.
[b]Total dietary fiber.
[c]Soluble dietary fiber expressed as a percentage, on a dry weight basis, of total dietary fiber.
[d]Brabender measurements were taken at 5% solids, and 92° C. for 10 minutes.
[e]Samples 29 were treated for 0.5 hours at 100° C. and then for 3.5 hours at 50° C.

EXAMPLE 2

This example illustrates the preparation of bleached, destarched tapioca fiber.

Part A

Destarched tapioca fiber samples were prepared by the method of Example 1, Part A, and subjected to the bleaching treatments described in Table III.

TABLE III

| Sample | Reagent | Reagent Level % | pH | Reaction Time (Hrs.) | Reaction Temp. (°C.) | Color of Product | Brabender[a] Viscosity (BU) |
|---|---|---|---|---|---|---|---|
| 30 | Ammonium Persulfate | 0.075 | 6.5 | 16 | 25 | Brown | — |
| 31 | Ammonium Persulfate | 5.0 | 6.5 | 16 | 25 | Brown | — |
| 32 | Ammonium Persulfate | 5.0 | 10.0 | 16 | 25 | Brown | — |
| 33 | Benzoyl Peroxide | 1.0 | 10 | 16 | 25 | Dark Brown | — |
| 34 | Benzoyl Peroxide | 3.0 | 10 | 16 | 25 | Dark Brown | — |
| 35 | Hydrogen Peroxide | 0.45 | 6.5 | 16 | 25 | Brown | — |
| 36 | Hydrogen Peroxide | 0.45 | 11.0 | 4 | 70 | Tan | — |
| 37 | Hydrogen Peroxide | 5.00 | 10.0 | 16 | 25 | Brown | — |
| 38 | Hydrogen Peroxide | 10.00 | 10.0 | 16 | 25 | Brown | — |
| 39 | Peracetic Acid | 1.00 | 7.0 | 16 | 25 | Tan | 50 |
| 40 | Potassium Permanganate | 0.50 | 10.0 | 16 | 30 | Brown | — |
| 41 | Potassium Permanganate | 5.00 | 5.5 | 16 | 25 | Dark Brown | — |
| 42 | Potassium Permanganate | 10.00 | 5.5 | 16 | 25 | Dark Brown | — |
| 43 | Potassium Permanganate | 3.00 | 10.0 | 16 | 25 | Tan | — |
| 44 | Potassium Permanganate | 5.00 | 10.0 | 16 | 25 | Dark Brown | — |
| 45 | Sodium Chlorite | 0.5 | 5 | 4 | 80 | Brown | — |
| 46 | Sodium Chlorite | 5.0 | 5 | 4 | 80 | Off White | — |
| 47 | Sodium Chlorite | 10.0 | 5 | 4 | 80 | White | — |
| 48 | Sodium Chlorite | 10.0 | 5 | 16 | 80 | White | — |
| 49 | Sodium Chlorite | 3.0 | 5 | 16 | 40 | Light Brown | — |
| 50 | Sodium Chlorite | 3.0 | 5 | 16 | 25 | Brown | — |
| 51 | Sodium Chlorite | 0.5 | 5 | 16 | 25 | Brown | — |
| 52 | Sodium Chlorite | 3.0 | 5.5 | 2 | 100 | Tan | 2400 |
| 53 | Sodium Chlorite | 3.0 | 5.5 | 2 | 100 | Tan | — |
| 54 | Sodium Chlorite | 3.0 | 5.5 | 2 | 100 | Tan | 3400 |
| 55 | Sodium Chlorite | 3.0 | 5.5 | 2 | 100 | Tan | 2900 |
| 56 | Sodium Chlorite | 3.0 | 5.5 | 2 | 80 | Tan | 360 |
| 57 | Sodium Chlorite | 3.0 | 5.5 | 2 | 100 | Tan | 3800 |
| 58 | Sodium Chlorite | 3.0 | 5.5 | 2 | 100 | Tan | 60 |
| 59 | Sodium Chlorite | 3.0 | 5.5 | 2 | 80 | Tan | 3800 |
| 60 | Sodium Chlorite | 3.0 | 5.5 | 2 | 80 | Tan | 4450 |
| 61 | Sodium Chlorite | 0.5 | 5.5 | 2 | 80 | Tan | 2800 |
| 62 | Sodium Chlorite | 3.0 | 5.5 | 2 | 80 | Tan | — |
| 63 | Sodium Chlorite | 3.0 | 5.5 | 2 | 80 | Tan | 2800 |
| 64 | Sodium Hypochlorite | 5.5 | 11 | 2 | 25 | Light Tan | — |
| 65 | Sodium Hypochlorite | 5.5 | 11 | 4 | 25 | Light Tan | — |
| 66 | Sodium Hypochlorite | 5.5 | 11 | 6 | 25 | Off White | — |
| 67 | Sodium Hypochlorite | 5.5 | 11 | 8 | 25 | Off White | — |
| 68 | Sodium Hypochlorite | 5.5 | 11 | 12 | 25 | Off White | — |
| 69 | Sodium Hypochlorite | 5.5 | 11 | 12 | 25 | Off White | — |
| 70 | Sodium Hypochlorite | 5.5 | 11 | 16 | 25 | Off White | — |

[a]Brabender measurements were made by the method of Example 1.

The results of the bleaching treatments are shown in Table III. None of the treatments with ammonium persulfate or benzoyl peroxide produced a satisfactory level of fiber color reduction. Potassium permanganate lightened the tapioca fibers when used at 3%, but not at 0.5, 5.0 or 10%.

Other reagents, including hydrogen peroxide, peracetic acid, sodium chlorite and sodium hypochlorite, effectively bleached tapioca fiber. Hydrogen peroxide was effective only at higher temperature and pH levels (e.g., 70° C. and pH=11.0). Higher reagent concentrations and temperatures were more effective when sodium chlorite was used as the bleaching agent.

Part B

The effect of bleaching on fiber contents (total and soluble dietary fiber), water holding capacity and other qualities of the tapioca fibers were measured. Results are shown in Table IV, below.

WATER HOLDING CAPACITY

Water holding capacity of the tapioca fiber was measured by the "Net Test" method of Hermansson, A. M., and Lucisano, M., "Gel Characteristics-Water Binding Properties of Blood Plasma Gels and Methodological Aspects on the Water Binding of Gel Systems", Journal of Food Science 1982, 47 (6) 1955-1959, 1964. In this method a weighed sample (0.2 to 0.3 g) of fiber was placed on a net in the middle of a tared centrifuge cylinder (obtained from AgriPilot and designed for use in a Size 1 Model CM centrifuge obtained from International Equipment Company, Neeham Heights, Massachusetts) and hydrated with an excess of a weighed aliquot of distilled water for 20 minutes. The cylinder was assembled and the sample was centrifuged for 10 minutes at 1,000 rpms. The upper cup of the cylinder containing the bound water and the sample was weighed and the water holding capacity (WHC) was calculated as g bound water/g sample.

TABLE IV

| | | EFFECTS OF BLEACHING OF TAPIOCA FIBER | | | | | | | |
|---|---|---|---|---|---|---|---|---|---|
| Sample[a] | Reagent | Reagent Level[g] % | Reaction Time (Hrs.) | Reaction Temp. (°C.)[f] | Brabender[b] Viscosity (BU) | Starch % (dry wt) | TDF %[c] (dry wt) | SDF %[d] (of TDF) | WHC[e] |
| 52 | Sodium Chlorite | 3.0 | 2 | 100 | 2,400 | — | 75.8 | — | — |
| 53 | Sodium Chlorite | 3.0 | 2 | 100 | — | — | — | — | 4.0 |
| 54 | Sodium Chlorite | 3.0 | 2 | 100 | 3,400 | — | 86.6 | 14.0 | — |
| 55 | Sodium Chlorite | 3.0 | 2 | 100 | 2,900 | 2.3 | 83.2 | 12.0 | 3.9 |

TABLE IV-continued

EFFECTS OF BLEACHING OF TAPIOCA FIBER

| Sample[a] | Reagent | Reagent Level[g] % | Reaction Time (Hrs.) | Reaction Temp. (°C.)[f] | Brabender[b] Viscosity (BU) | Starch % (dry wt) | TDF %[c] (dry wt) | SDF %[d] (of TDF) | WHC[e] |
|---|---|---|---|---|---|---|---|---|---|
| 56 | Sodium Chlorite | 3.0 | 2 | 80 | 360 | — | — | — | — |
| 57 | Sodium Chlorite | 3.0 | 2 | 100 | 3,800 | 7.0 | — | — | — |
| 58 | Sodium Chlorite | 3.0 | 2 | 100 | 60 | 3.1 | — | — | — |
| 59 | Sodium Chlorite | 3.0 | 2 | 80 | 3,800 | 8.0 | — | — | — |
| 60 | Sodium Chlorite | 3.0 | 2 | 80 | 4,450 | 2.1 | 87.2 | 17.7 | 4.1 |
| 60A | Sodium Chlorite | 3 | 2 | 100 | 20 | 11.0 | 86.0 | 11.0 | — |
| 60B | Sodium Chlorite | 3 | 2 | 100 | 250 | 11.9 | — | — | 2.7 |
| 60C | Sodium Chlorite | 3 | 2 | 100 | 2,900 | 6.7 | 81.0 | 11.3 | 3.9 |
| 60D | Sodium Chlorite | 3 | 2 | 100 | 1,400 | 2.3 | 86.2 | 20.1 | 3.4 |
| 60E | Sodium Chlorite | 3 | 2 | 100 | 3,400 | — | 83.7 | 15.9 | — |
| 60F | Sodium Chlorite | 3 | 2 | 100 | 3,500 | 2.1 | 87.3 | 20.3 | 3.5 |
| 71 | Sodium Hypochlorite | 5.0 | 16 | 40–25 | 4,000 | 12.9 | — | — | — |
| 72 | Sodium Hypochlorite | 5.0 | 16 | 40–25 | 100 | — | — | — | — |
| 73 | Sodium Hypochlorite | 5.0 | 16 | 80–25 | 1,000 | — | — | — | — |
| 74 | Sodium Hypochlorite | 5.0 | 16 | 80–25 | 100 | — | — | — | — |
| 75 | Sodium Hypochlorite | 5.5 | 16 | 40–25 | — | 10.7 | 65.4 | 20.9 | — |
| 76 | Sodium Hypochlorite | 5.5 | 16 | 40–25 | 3,800 | 17.2 | — | — | 5.2 |
| 77 | Sodium Hypochlorite | 5.5 | 16 | 80–25 | 3,800 | 12.8 | — | — | 5.1 |
| 78 | Sodium Hypochlorite | 5.5 | 16 | 40–25 | 3,800 | 11.8 | — | — | 4.9 |
| 79 | Sodium Hypochlorite | 5.5 | 16 | 80–25 | 3,000 | 10.6 | — | — | 6.6 |
| 80 | Sodium Hypochlorite | 5.5 | 16 | 40–25 | — | — | — | — | — |
| 81 | Sodium Hypochlorite | 5.5 | 16 | 40–25 | — | 5.0 | 91 | 17.9 | — |
| 82 | Sodium Hypochlorite | 5.5 | 4 | 40–25 | 1,200 | 13.0 | 75 | <1 | 4.0 |
| 83 | Sodium Hypochlorite | 5.5 | 6 | 40–25 | 3,000 | 10.7 | 79 | 9.3 | 4.4 |
| 84 | Sodium Hypochlorite | 5.5 | 8 | 40–25 | 2,000 | 12.6 | 71 | 8.3 | 5.7 |
| 85 | Sodium Hypochlorite | 11.0 | 8 | 40–25 | 70 | — | — | — | — |
| 86 | Sodium Hypochlorite | 5.5 | 16 | 25 | 80 | 20.1 | — | — | — |
| 87 | Sodium Hypochlorite | 5.5 | 6 | 40–25 | 3,600 | 2.3 | — | — | — |
| 88 | Sodium Hypochlorite | 5.5 | 4 | 40–25 | — | 1.4 | 90.5 | 27.8 | — |
| 89 | Sodium Hypochlorite | 5.5 | 6 | 40–25 | — | 1.4 | 89.9 | 14.5 | — |
| 90 | Sodium Hypochlorite | 5.5 | 8 | 40–25 | — | 1.4 | 88.8 | 18.3 | — |

[a]Samples were destarched by the method of Example 1, Part A. Samples 52–60 were bleached at pH = 5.5; samples 71–90 at pH = 11.0.
[b]Brabender measurements were made by the method of Example 1.
[c]Total dietary fiber.
[d]Soluble dietary fiber expressed as a percentage, on a dry weight basis, of total dietary fiber.
[e]Water holding capacity, measured by the method of Example 2.
[f]First temperature is starting temperature of reaction. Where a second temperature is indicated, samples were then allowed to cool to second temperature.
[g]Reagent percentages represent active chlorine on a fiber weight basis.

The results show that samples bleached at higher temperatures (e.g. >80° C.) contain less soluble dietary fiber (SDF). When sodium hypochlorite was used as the bleaching reagent, the best bleaching effects were observed in samples which were cooled to 40° C. after destarching and then bleached for 6 hours. Sufficient sodium hypochlorite to yield 5.5% active chlorine (on a fiber weight basis) at a pH of 11 provided a whitened fiber. Samples prepared with sodium hypochlorite tended to lose SDF in bleaching treatments conducted for more than 4 hours. Actual amounts of SDF also varied depending on the starch content, particle size and fiber variables other than the bleaching treatment. Sodium hypochlorite reagent was preferred over sodium chlorite because lower temperatures (25°–40° C. versus 80° C.) were effective to bleach the fiber.

Brabender viscosities were affected by fiber drying method, particle size and starch content, but were not affected significantly by the bleaching treatment. Acceptable viscosities were observed in sodium hypochlorite treated samples which were bleached at pH=11 for 6 hours.

Water holding capacity of the fiber samples generally increased as the duration of the bleaching treatment increased.

Part C

The effect of particle size on water holding capacity and Brabender viscosity was measured using the testing methods described above.

A destarched, tapioca fiber sample (destarched with alpha-amylase for 4 hours at 80° C. to yield a product containing 1.6% starch) was ground to provide samples having the following particle size characteristics.

Sample A: 95% through a U.S.S.S. 20 mesh screen and on a retained U.S.S.S. 40 mesh screen;
Sample B: 95% through a U.S.S.S. 40 mesh screen and retained on a U.S.S.S. 100 mesh screen;
Sample C: 95% through a U.S.S.S. 100 mesh screen and retained on a U.S.S.S. 270 mesh screen;

Results are shown in Table V, below.

TABLE V

| | Effect of Particle Size | |
|---|---|---|
| Sample[a] | Brabender[b] Viscosity (Bu) | WHC[c] |
| A | 3,200 | 3.8 |
| B | 2,000 | 3.6 |
| C | 20 | 4.0 |

[a]Refined tapioca fiber samples were prepared according to Example 2, Part A and Part C.
[b]Brabender measurements were taken at 5% solids and 95° C. for 10 minutes.
[c]Water holding capacity was measured according to method of Example 2, Part B, above.

These results show that the viscosity decreases with a decrease in particle size. The water holding capacity increases as the viscosity and particle size decrease. Thus, particle size may be adjusted so that the fiber provides functional properties suited to particular food applications.

EXAMPLE 3

This example illustrates the preparation of bread employing destarched and bleached tapioca fiber and unrefined tapioca fiber. Bread was prepared according to the following formulation and procedure.

BREAD FORMULATION

| | Fiber Sources[a] | | | | | | | | | | | |
|---|---|---|---|---|---|---|---|---|---|---|---|---|
| | Control | | Tapioca | | Potato | | Beet | | Wheat Bran | | Oat Bran | |
| Ingredient | g | % | g | % | g | % | g | % | g | % | g | % |
| Flour | 232 | 47.0 | 192 | 30.1 | 186.7 | 29.3 | 186.7 | 29.3 | 154.7 | 24.2 | 19.5 | 3.1 |
| Sugar | 40 | 8.1 | 40 | 6.3 | 40 | 6.3 | 40 | 6.3 | 40 | 6.3 | 40 | 6.3 |
| Non-fat Dry Milk | 14 | 2.8 | 14 | 2.2 | 14 | 2.2 | 14 | 2.2 | 14 | 2.2 | 14 | 2.2 |
| Salt | 14 | 2.8 | 14 | 2.2 | 14 | 2.2 | 14 | 2.2 | 14 | 2.2 | 14 | 2.2 |
| Shortening | 14 | 2.8 | 14 | 2.2 | 14 | 2.2 | 14 | 2.2 | 14 | 2.2 | 14 | 2.2 |
| Vital Wheat Gluten | — | — | 24 | 3.8 | 24 | 3.8 | 24 | 3.8 | 24 | 3.8 | 24 | 3.8 |
| Water | 180 | 36.4 | 300 | 47.0 | 300 | 47.0 | 300 | 47.0 | 300 | 47.0 | 300 | 47.0 |
| Fiber | — | — | 40 | 6.3 | 45.3 | 7.1 | 45.3 | 7.1 | 77.3 | 12.1 | 212.5 | 33.3 |

[a]Dietary fiber sources were adjusted to give the same TDF level in the bread formulation. Fibers used were tapioca fiber (Sample 52 from Example 2, Part A, above, containing 76% TDF); potato fiber (Potex ™, 75% TDF, obtained from AgriPilot); beet fiber (75% TDF, obtained from Delta Fibre Foods); wheat bran (44% TDF, obtained from Lauhoff Grain Company); and oat bran (16% TDF, obtained from National Oats Company).

Bread was prepared by making a sponge from 450 g flour, 7 g yeast food, 20 g yeast and 240 g water, mixing the sponge for one minute at low speed and 4 minutes at medium speed in a Hobart Mixer, and letting the sponge ferment for 1 to 1½ hours at 85° F. (29.4° C.) until doubled in volume.

The bread formulation ingredients were mixed for one minute, the sponge was cooled, and the sponge was mixed with the other ingredients for 10 minutes on low speed to form a dough. The dough was formed into loaves, proofed at 100° F. (43° C.) and 85% relative humidity for 31 minutes, then baked at 440°–450° F. (227°–232° C.) for 16 minutes.

All fiber samples, except the oat bran fiber, produced acceptable bread, with similar loaf volume and moisture content. The oat bran produced a smaller volume loaf. A second tapioca fiber sample (unrefined tapioca fiber containing 9.6% moisture and 26% TDF, obtained from National Starch & Chemical (Thailand) Ltd., Bangkok, Thailand) also produced acceptable bread.

EXAMPLE 4

This example illustrates the preparation of donuts employing tapioca fiber. The following formulation and procedures were used to make donuts.

DONUT FORMULATION

| | Quantity | | | |
|---|---|---|---|---|
| | Control | | Experimental | |
| Ingredient | g | % | g | % |
| Egg | 50 | 10.7 | 50 | 10.7 |
| Shortening | 10 | 2.1 | 10 | 2.1 |
| Milk | 92 | 19.6 | 92 | 19.6 |
| Flour | 210 | 44.8 | 199.5 | 42.5 |
| Baking Powder | 12 | 2.6 | 12 | 2.6 |
| Tapioca Fiber[a] | 0 | 0 | 10.5 | 2.2 |
| A Destarched | | | | |
| B Unrefined | | | | |
| C Destarched and Bleached | | | | |

[a]Tapioca fiber Sample A was prepared by treating tapioca pulp with 1% alpha-amylase for 4 hours at 80° C. Sample C was prepared by treating pulp with 1% alpha-amylase for 4 hours at 80° C. and then bleaching the pulp with a solution of sodium hypochlorite (comprising 5% active chlorine at a pH of 10) for 6 hours at room temperature. Sample B was the unrefined tapioca pulp fiber used as starting material to prepare Sample A and C. The unrefined fiber was obtained from National Starch & Chemical (Thailand) Ltd., Bangkok, Thailand.

The tapioca fiber Samples A and C used in the donuts were destarched by the method of Example 1, Part A, and bleached with sodium hydrochlorite. Tapioca fiber was hydrated in excess water for 5 minutes before adding it to the donut mix. Donuts were prepared by blending all dry ingredients except for tapioca fiber, and then adding tapioca fiber that had been hydrated in excess water for minutes. The milk was added, a dough was formed and then rolled out. The rolled dough was cut with a donut cutter. Donuts were fried in oil at 310° F. (160° C.) for minute, 30 seconds, on one side and 1 minute, 15 seconds, on the other side.

Donuts were weighed before and after cooking to determine oil pick-up and the percent moisture was measured before cooking. Results are shown in Table VI.

TABLE VI

DONUT EVALUATIONS

| Sample | Weight (g) Before & After Cooking | | % Oil Pick-up | % Moisture | % Fat[a] |
|---|---|---|---|---|---|
| Control Tapioca Fiber | 35.8 | 44.85 | 25.3 | 11.6 | 30.8 |
| A | 38.76 | 41.98 | 8.3 | 17.8 | 22.8 |
| B | 33.05 | 36.71 | 11.1 | 14.6 | — |
| C | 31.65 | 33.54 | 6.0 | 16.4 | — |

[a]Percent fat was tested by AOAC Methods 7.063 and 24.009, Official Methods of Analysis of the Association of Official Analytical Chemists 14th Edition, 1984.

An organoleptic evaluation of the donuts for flavor and texture showed the tapioca fiber-containing donuts were acceptable when compared to the control.

EXAMPLE 5

This example illustrates the preparation of cereals employing tapioca fiber.

Part A

Hot cereals were prepared according to the following formulation and procedure.

HOT CEREAL FORMULATION

| Ingredients | Percent by Weight Experimental |
|---|---|
| A. Oats[a] | 33.0 |
| QUICKSPERSE Starch[b] | 20.0 |
| Tapioca Fiber[c] | 15.0 |
| Sugar | 15.0 |
| Salt | 0.30 |
| Artificial apple flavor[d] | 0.20 |
| Cinnamon (ground) | 1.00 |

HOT CEREAL FORMULATION -continued

| Ingredients | Percent by Weight Experimental |
|---|---|
| Dried apple bits[e] | 15.35 |
| Malic Acid | 0.15 |
| (fine, granular) | 100 |
| B. Water | 155 |

[a]Quick Oats, obtained from Quaker Oats Co., Chicago, Illinois.
[b]Starch obtained from National Starch and Chemical Company, Bridgewater, New Jersey.
[c]Unrefined tapioca fiber containing 33–36% TDF.
[d]Obtained from Firmenich, Inc., Princeton, New Jersey.
[e]Obtained from Sunmaid Growers of California, Pleasanton, California.

Cereal was prepared by dry blending the ingredients in A, adding the water in B and stirring to mix. The cereal was heated until thick (3 minutes on high heat).

The flavor and texture of the tapioca fiber-containing cereal were acceptable when compared to the following commercially available cereals: Wheatena ® cereal (obtained from American Home Foods, Inc., New York, N.Y.), Farina ® cereal (obtained from The Pillsbury Co., Minneapolis, Minn.), and Oatbran Hot Cereal (obtained from Hardy Life National Foods, Inc.).

Part B

Extruded flaked wheat cereals were prepared according to the following formulation and procedures, Ingredients were fed into the extruder at the above conditions (See FIG. 2). In some cases, the ingredients had to be fed into the extruder using three separate feeds. This was necessary due to the contrasting bulk densities of the wheat flakes, the fibers, and the sugar-salt blend. In the instances when two feeders were used, the wheat flakes were fed in with one feeder and the sugar, salt and fiber were blended together and fed into the extruder with a second feeder.

After steady state conditions were obtained, samples were taken in the form of fifteen inch extrudate ropes. A half-product (i.e., moist pellet) was made by cutting the ropes into pellets approximately ¼ inch long.

Flakes were made by taking the half-products and placing them on the outer edges of a Teflon ® plate. Approximately one inch was left between each half-product and the outer edge of the plate. This allowed enough room for the pellet to be flattened (compressed) into a flake. A second Teflon ® plate was placed on top of the pellets. The plates were placed in a hydraulic press and 500–2000 psi of pressure was applied.

The pressed flakes were placed in an aluminum baking tray and toasted in a conventional oven at 200°–210° C. for a period of 2 to 10 minutes. The aluminum baking tray was modified by puncturing holes in the bottom of the pan to insure uniform toasting. After toasting, the samples were placed in sealed glass jars to await evaluation. Final flake moisture was 3–5%.

WHEAT FLAKE CEREAL FORMULATION

| | Percent by Weight | | |
|---|---|---|---|
| Ingredient | Control | Destarched Tapioca Fiber[b] | Unrefined Tapioca Fiber[c] |
| Wheat Flakes | 87.2 | 69.2 | 60.2 | 44.2 |
| Sugar | 8.7 | 8.7 | 8.7 | 8.7 |
| Salt | 2.4 | 2.4 | 2.4 | 2.4 |
| Malt Syrup[a] | 1.6 | 1.6 | 1.6 | 1.6 |
| Trisodium Phosphate | 0.1 | 0.1 | 0.1 | 0.1 |
| Fiber | 0.0 | 18.0 | 27.0 | 43.0 |
| Total | 100.0 | 100.0 | 100.0 | 100.0 |
| TDF (g/1 ounce serving) | — | 4 | 6 | 4 |

[a]50% solids syrup.
[b]Tapioca fiber was destarched by the method of Example 1, Part A, and contained 80% TDF.
[c]Unrefined tapioca fiber contained 9.6% moisture and 33–36% TDF.

To prepare a 2,000 or a 5,000 g batch of cereal, all of the dry ingredients except the wheat flakes and the fiber were weighed out, charged into a one gallon jar, capped and set on the rollers at 100 rpm for at least three hours to insure sufficient blending. (The wheat flakes, fiber, and malt syrup were introduced into the process in a separate step from the dry blended ingredients).

The blended ingredients were fed into a twin-screw extruder (Model ZSK-30, obtained from Werner & Pfleiderer) under the conditions set forth below:

| Extruder Conditions for Producing Extruded Flakes | |
|---|---|
| Barrel Length: | 12 (L/D = 36) |
| Screw Configuration: | Sc 12-44 |
| Screw Speed: | 250–300 rpm |
| Die Diameter: | 2 × 4 rpm |
| Dry Feed Rate: | 10 kg/hour |
| Input Moisture: | 30% |
| Zone Temperatures: | 0/150/43/32/($H_2O$ °C. Cooled) |

Flaked extruded wheat cereals were also prepared from oat bran (National Oats Company, Cedar Rapids, Iowa), rice bran (Calbran, California Rice Bran, Inc., Redondo Beach, Calif.) and wheat bran (Lauhoff Grain Company, Danville, Ill.) as a fiber source at 18% of the cereal formulation. These cereals, the control and the tapioca fiber containing cereals were placed in milk and subjected to an organoleptic evaluation of flavor, odor and texture, including crunchiness, bowl-life and eating quality. The tapioca fiber samples (at 18% of formulation) compared favorably to the control and were preferred over the other fiber samples.

Part C

Extruded, expanded (puffed) oat cereals were prepared according to the following formulation and procedures.

| EXTRUDED EXPANDED CEREAL FORMULATION | | | |
|---|---|---|---|
| Ingredient | Control | Percent by Weight Destarched Tapioca Fiber[a] | Unrefined Tapioca Fiber[b] |
| Oat Flour | 70 | 56 | 36.4 |
| Corn Flour | 20 | 18 | 43 |
| Fiber | — | 16 | 10.6 |
| Sugar | 10 | 10 | 10 |
| Total | 100 | 100 | 100 |
| TDF (g/1 ounce serving | — | 4 | 4 |

[a]Tapioca fiber was destarched by the method of Example 1, Part A, and contained 80% TDF.
[b]Unrefined tapioca fiber contained 9.6% moisture and 33–36% TDF.

To prepare a 2,000 g batch of cereal, all of the ingredients were weighed out, charged into a one gallon jar and placed on rollers at 100 rpm to insure sufficient blending.

The blended ingredients were fed into a twin-screw extruder (Model ZSK-30, obtained from Werner & Pfleiderer), and extruded under the conditions set forth below:

| Extruded Conditions for Producing Expanded Cereal | |
|---|---|
| Barrel Length: | 5 (L/D = 15) |
| Screw Configuration: | Sc 5-18 |
| Screw Speed: | 250–390 rpm |
| Die Diameter: | 2 × 4 mm |
| Dry Feed Rate: | 13.3 kg/hour |
| Input Moisture: | 6.4–9.4% |
| Zone Temperatures: | 0/0/60/150/140° C. |

Samples were taken in the form of extrudate ropes after steady state conditions were obtained. The ropes were the cut into pieces approximately ½ inch long. Using a set of dial calipers, diameter readings were taken on the samples. The average diameter of 10 samples containing tapioca fiber was 0.302 inch, about 8% more expansion than the control (0.280 inch). The samples were placed in an aluminum baking tray and toasted in a conventional oven at 200°–210° C. for a period of 3 to 5 minutes. After toasting, the cereals were placed in milk and subjected to organoleptic evaluation of flavor, odor and texture, including crunchiness, bowl-life and expansion. The tapioca fiber samples compared favorably to the control. Samples of cereals containing the fibers (oat, rice and wheat bran) described in Part B, above, were prepared and compared to the tapioca fiber samples. The tapioca fiber samples were preferred in organoleptic evaluations. Additionally, the other fiber sources yielded average diameters in cereal pieces that ranged from about 0 to 14% less than the control (0.240 to 0.254 inch).

These results shows that in contrast to other fibers, tapioca fiber improves extruded cereal texture.

Now that the preferred embodiments of the present invention have been described in detail, various modifications and improvements thereon will become readily apparent to those skilled in the art. Accordingly, the scope and spirit of the invention are to be limited only by the claims and not by the foregoing specification.

We claim:

1. A dietary fiber of tapioca origin, comprising on a dry solids basis, at least 70% total dietary fiber, of which at least 12% is soluble dietary fiber, and less than 15% starch, wherein the dietary fiber has a water-holding capacity of at least 2.5 and a viscosity of at least 100 B.U. in a 5% aqueous solution.

2. The dietary fiber of claim 1, wherein the fiber is refined by bleaching with a reagent selected from the group consisting of hydrogen peroxide, sodium chlorite, sodium hypochlorite and potassium permanganate.

3. The dietary fiber of claim 1, wherein 50% of the fiber passes through a 40 mesh screen.

4. A process for refining tapioca pulp for use as a nutritional ingredient in nutritionally fortified processed foods, comprising the steps:

a) forming a slurry of 5 to 10%, by weight, ground tapioca pulp in an aqueous media;

b) enzymatically treating the slurry with a 1,4-alpha-D-glucosidase to depolymerize sufficient starch to yield a tapioca fiber containing less than 15% starch;

c) separating the tapioca fiber from the slurry; and d) washing the tapioca fiber to provide a refined tapioca fiber, wherein the refined tapioca fiber contains at least 70% total dietary fiber, of which at least 12% is soluble dietary fiber, and the refined tapioca fiber has a water-holding capacity of at least 2.5 and a viscosity of at least 100 B.U. in a 5% aqueous solution.

5. The process of claim 4, wherein the enzyme is an alpha-amylase or a glucoamylase.

6. The process of claim 5, wherein the enzymatic treatment of a 5-10%, by weight, aqueous slurry of tapioca pulp is conducted for 3 to 5 hours at 25° to 85° C., employing an alpha-amylase.

7. The process of claim 6, wherein the refined tapioca fiber comprises no more than 10%, by weight, starch and at least 75%, by weight, total dietary fiber, of which at least 15% is soluble dietary fiber.

8. The process of claim 4, further comprising the step of drying the tapioca fiber to a moisture content of less than 15%, by weight.

9. The process of claim 8, further comprising the step of adjusting the particle size of the tapioca fiber so that 95%, by weight, of the tapioca fiber passes through a U.S.S.S. 100 mesh screen.

10. The process of claim 4, further comprising the step of bleaching the tapioca fiber with a reagent selected from the group consisting of hydrogen perioxide, sodium chlorite, sodium hypochlorite and potassium permanganate.

11. The process of claim 10, wherein the reagent is sodium hypochlorite and a 5 to 10%, by weight, slurry of tapioca fiber is bleached for 5 to 6 hours at 25° to 40° C. at an alkaline pH.

12. The process of claim 11, further comprising the step of drying the bleached tapioca fiber to a moisture content of less than 15%, by weight.

13. A nutritionally-fortified, fiber-containing food comprising about 1 to 43%, by weight, of at least one dietary fiber of tapioca origin selected from the group consisting of unrefined tapioca fiber, refined tapioca fiber, comprising on a dry starch solids basis no more than 15% starch and at least 70%, by weight, total dietary fiber, of which at least 12% is soluble dietary fiber, wherein the refined tapioca fiber has a water-holding capacity of at least 2.5 and a viscosity of at least 100 B.U. in a 5% aqueous solution, and bleached, refined tapioca fiber comprising on a dry solids basis no more than 15% starch and at least 70%, by weight, total dietary fiber, of which at least 12% is soluble dietary fiber, wherein the bleached refined tapioca fiber has a water-holding capacity of at least 2.5 and a viscosity of at least 100 B.U. in a 5% aqueous solution.

14. The food of claim 13 wherein the food is selected from the group consisting of bread and other baked goods, fried foods, breaded and coated foods and cereals.

15. The food of claim 14, wherein one serving of the food comprises at least 4 grams of total dietary fiber, of which fiber at least 10%, by weight, is soluble dietary fiber.

* * * * *